(12) United States Patent
Takagi et al.

(10) Patent No.: US 6,579,679 B1
(45) Date of Patent: Jun. 17, 2003

(54) METHOD FOR EXAMINING CENTRAL NERVOUS SYSTEM DISEASES AND METHOD FOR SCREENING REMEDIES

(75) Inventors: Tsutomu Takagi, Minoo (JP); Naoya Sato, Suita (JP); Masaya Tohyama, Toyonaka (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/700,847
(22) PCT Filed: May 20, 1999
(86) PCT No.: PCT/JP99/02627
§ 371 (c)(1),
(2), (4) Date: Nov. 21, 2000
(87) PCT Pub. No.: WO99/60122
PCT Pub. Date: Nov. 25, 1999

(30) Foreign Application Priority Data

May 21, 1998 (JP) ............................................. 10-139408

(51) Int. Cl.[7] ........................... C12Q 1/68; C12P 19/34; C07K 14/435; C07H 21/02; C07H 21/04
(52) U.S. Cl. ......................... 435/6; 435/91.1; 435/91.2; 530/350; 536/23.1
(58) Field of Search ............................... 435/5, 6, 91.1, 435/91.2; 530/350; 935/71.1, 71.2; 536/23.1

(56) References Cited

PUBLICATIONS

Clark et al., Nature Genetics, vol. 11, pp. 219–222, Oct. 1995.
Anwar et al., Journal of Neurochemistry, vol. 66, pp. 1774–1777, 1996.
Levy–Lahad et al., Genomics vol. 34, pp. 198–204, 1996.
Levy–Lahad et al., Science vol. 269, pp. 973–977, 1995.
Rogaev et al., Nature vol. 376, pp. 775–778, 1995.
Jurgen Grunberg et al., "Truncated Presenilin 2 derived from differentially spliced mRNAs does not affect the ratio of amyloid β–peptide 1–42/1–40", Neuro Report (1998) vol. 9, No. 14 p.3292–3299.
Guy Prihar et al., "Structure and alternative splicing of the presenilin–2 gen", Neuro Report (1996) vol. 7, No. 10 p.1680–1684.

*Primary Examiner*—Stephanie Zitomer

(57) ABSTRACT

The present invention relates to a method for screening and identifying therapeutic agents or preventive agents for central nervous system diseases which comprises assaying a suppressing effect of a test substance on an expression of a splicing variant transcribed from presenilin-2 gene and to a method for examining central nervous system diseases which comprises detecting an expression of a splicing variant transcribed from presenilin-2 gene in a test sample originated from an animal individual.

7 Claims, 3 Drawing Sheets

Fig. 3

|  |  |  |
|---|---|---|
| exon 1 | GCATTTCCAG CAGTGAGGAG ACAGCCAGAA GCAAGCTATT GGAGCTGAAG GAACCTGAGA | 60 |
|  | CAGAAGCTAG TCCCCCCTCT GAATTTTACT GATGAAGAAA CTGAGGCCAC AGAGCTAAAG | 120 |
|  | TGACTTTTCC CAAGGTCGCC CAGCGAGGAC GTGGGACTTC TCAGACGTCA GGAGAGTGAT | 180 |
| exon 2 | GTGAGGGAGC TGTGTGACCA TAGAAAGTGA CGTGTTAAAA ACCAGCGCTG CCCTCTTTGA | 240 |
|  | AAGCCAGGGA GCATCATTCA TTTAGCCTGC TGAGAAGAAG AAACCAAGTG TCCGGGATTC | 300 |
|  | AGACCTCTCT GCGGCCCCAA GTGTTCGTGG TGCTTCCAGA GGCAGGGCTA TGCTCACATT | 360 |
| exon 3 | CATGGCCTCT GACAGCGAGG AAGAAGTGTG TGATGAGCGG ACGTCCCTAA TGTCGGCCGA | 420 |
|  | GAGCCCCACG CCGCGCTCCT GCCAGGAGGG CAGGCAGGGC CCAGAGGATG GAGAGAACAC | 480 |
|  | TGCCCAGTGG AGAAGCCAGG AGAACGAGGA GGACGGTGAG GAGGACCCTG ACCGCTATGT | 540 |
| exon 4 | CTGTAGTGGG GTTCCCGGGC GGCCGCCAGG CCTGGAGGAA GAGCTGACCC TCAAATACGG | 600 |
|  | AGCGAAGCAC GTGATCATGC TGTTTGTGCC TGTCACTCTG TGCATGATCG TGGTGGTAGC | 660 |
|  | CACCATCAAG TCTGTGCGCT TCTACACAGA GAAGAATGGA CAGCTCATCT ACACGACATT | 720 |
| exon 5 | CACTGAGGAC ACACCCTCGG TGGGCCAGCG CCTCCTCAAC TCCGTGCTGA ACACCCTCAT | 780 |
|  | CATGATCAGC GTCATCGTGG TTATGACCAT CTTCTTGGTG GTGCTCTACA AGTACCGCTG | 840 |
| exon 6 | CTACAAGTTC ATCCATGGCT GGTTGATCAT GTCTTCACTG ATGCTGCTGT TCCTCTTCAC | 900 |
|  | CTATATCTAC CTTGGGGAAG TGCTCAAGAC CTACAATGTG GCCATGGACT ACCCCACCCT | 960 |
| exon 7 | CTTGCTGACT GTCTGGAACT TCGGGGCAGT GGGCATGGTG TGCATCCACT GGAAGGGCCC | 1020 |
|  | TCTGGTGCTG CAGCAGGCCT ACCTCATCAT GATCAGTGCG CTCATGGCCC TAGTGTTCAT | 1080 |
|  | CAAGTACCTC CCAGAGTGGT CCGCGTGGGT CATCCTGGGC GCCATCTCTG TGTATGATCT | 1140 |
|  | CGTGGCTGTG CTGTGTCCCA AAGGGCCTCT GAGAATGCTG GTAGAAACTG CCCAGGAGAG | 1200 |
| exon 8 | AAATGAGCCC ATATTCCCTG CCCTGATATA CTCATCTGCC ATGGTGTGGA CGGTTGGCAT | 1260 |
| exon 9 | GGCGAAGCTG GACCCCTCCT CTCAGGGTGC CCTCCAGCTC CCCTACGACC GGAGATGGA | 1320 |
| exon 10 | AGAAGACTCC TATGACAGTT TTGGGGAGCC TTCATACCCC GAAGTCTTTG AGCCTCCCTT | 1380 |
|  | GACTGGCTAC CCAGGGGAGG AGCTGGAGGA AGAGGAGGAA AGGGGCGTGA AGCTTGGCCT | 1440 |
| exon 11 | CGGGGACTTC ATCTTCTACA GTGTGCTGGT GGGCAAGGCG GCTGCCACGG GCAGCGGGGA | 1500 |
|  | CTGGAATACC ACGCTGGCCT GCTTCGTGGC CATCCTCATT GGCTTGTGTC TGACCCTCCT | 1560 |
|  | GCTGCTTGCT GTGTTCAAGA AGGCGCTGCC CGCCCTCCCC ATCTCCATCA CGTTCGGGCT | 1620 |
|  | CATCTTTTAC TTCTCCACGG ACAACCTGGT GCGGCCGTTC ATGGACACCC TGGCCTCCCA | 1680 |
| exon 12 | TCAGCTCTAC ATCTGAGGGA CATGGTGTGC CACAGGCTGC AAGCTGCAGG GAATTTTCAT | 1740 |
|  | TGGATGCAGT TGTATAGTTT TACACTCTAG TGCCATATAT TTTAAGACT TTTCTTTCCT | 1800 |
|  | TAAAAAATAA AGTACGTGTT TACTTGGTGA GGAGGAGGCA GAACCAGCTC TTTGGTGCCA | 1860 |
|  | GCTGTTTCAT CACCAGACTT TGGCTCCCGC TTTGGGGAGC GCCTCGCTTC ACGGACAGGA | 1920 |
|  | AGCACAGCAG GTTTATCCAG ATGAACTGAG AAGGTCAGAT TAGGGCGGGG AGAAGAGCAT | 1980 |
|  | CCGGCATGAG GGCTGAGATG CGCAAAGAGT GTGCTCGGGA GTGGCCCCTG GCACCTGGGT | 2040 |
|  | GCTCTGGCTG GAGAGGAAAA GCCAGTTCCC TACGAGGAGT GTTCCCAATG CTTTGTCCAT | 2100 |
|  | GATGTCCTTG TTATTTTATT GCCTTTAGAA ACTGAGTCCT GTTC | 2144 |

Fig. 4

```
       exon 2                                          intron
ATTCAGACCT CTCTGCGGCC CCAAGTGTTC GTGCAGGTCC AAAATCACTC AAGGTGGGGA
GCCTCGAGGA GCAGTCAGGG CCGGGAGCAT CAGCCCCTTG CCTTCTCCCT CAGCATCTAC  exon 5
ACGCCATTCA CTGAGGACAC ACCCTCGGTG GGCCAGCGCC TCCTCAACTC CGTGCTGAAC
ACCCTCATCA TGATCAGCGT CATCGTGGTT ATGACCATCT TCTTGGTGGT GCTCTACAAG
TACCGCTGAT ACAAGTTCAT CCATGGCTGG TTGATCATGT CTTCACTGAT GCTGCTGTTC
CTCTTCACCT ATATCTACGT TGGGGAAGTG CTCAAGACCT ACAATGTGGC CATGGACTAC
CCCACCCTCT AGCTGACTGT CTGGAACTTC GGGGCAGTGG GCATGGTGTG CATCCACTGG
AAGGGCCCTC TGGTGCTGCA GCAGGCCTAC CTCATCATGA TCAGTGCGCT CATGGCCCTA
GTGTTCATCA AGTACCTCCC AGAGTGGTCC
```

Fig. 5

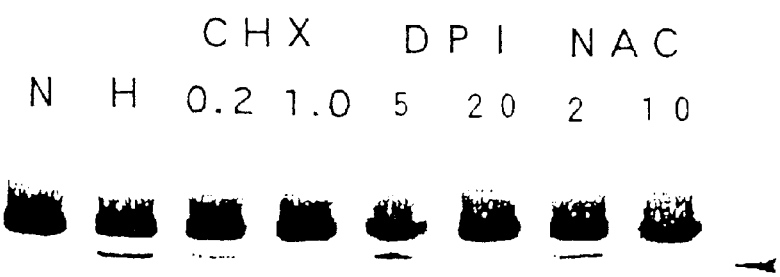

```
              CHX      DPI     NAC
   N  H    0.2 1.0    5  20   2  10
```

МETHOD FOR EXAMINING CENTRAL NERVOUS SYSTEM DISEASES AND METHOD FOR SCREENING REMEDIES

This application is the national phase under 35 U.S.C. §371 of PCT International Application No. PCT/JP99/02627 which has an International filing date of May 20, 1999, which designated the United States of America.

TECHNICAL FIELD

The present invention relates to a novel splicing variants of presenilin-2 along with a method for screening and a method for identifying therapeutic agents for central nervous system diseases. The present invention also relates to a method for examining central nervous system diseases.

BACKGROUND ART

In the genome DNA of eucaryotes, sequences corresponding to mature mRNA are frequently present separated at several locations. In such cases, gene transcription is performed continuously over the entire region, including those sequences corresponding to mature mRNA, resulting in the production of precursor mRNA (pre-mRNA) (transcription products also containing portions not required by mature mRNA). This precursor mRNA is then subjected to processing to become mature mRNA. During the course of processing, simultaneous to the addition of a cap structure and poly A, those portions not required by the mRNA (introns or intervening sequences) are cut out, while the portions corresponding to the mature mRNA (exons) are joined to form mature mRNA. These cuttting and joining processes are referred to as "splicing". Splicing is a complicated and delicate process in which a plurality of severing and coupling processes are regulated by the involvement of a large protein-RNA aggregate referred to as a spliceosome. For example, although different types of mature mRNA, namely "splicing variants", are frequently formed due to a mutation and so forth that occurs in the boundary region between an intron and exon on the genome, some of these variants are known to give rise to functionally abnormal mutant proteins that are capable of causing disease. Research has been conducted thus far on splicing variants in causative genes in order to elucidate the mechanism of pathogenesis for various diseases and disorders, and splicing variants have also been used as diagnostic markers for certain diseases.

On the other hand, the amyloid precursor protein (APP) gene on chromosome 21, the presenilin-1 (PS-1) gene on chromosome 14 and the presenilin-2 (PS-2) gene on chromosome 1 have been previously determined to be the major causative genes of familial Alzheimer's disease (FAD). Subsequently, research has been conducted while focusing on mutations and splicing variants and so forth discovered in these causative genes on the relationship between these and the mechanism of pathogenesis of Alzheimer's disease. However, very little has been determined for the mechanism of pathogenesis of sporadic Alzheimer's disease, which constitutes the majority of Alzheimer's disease.

For example, mRNA originating in the brain tissue of familiar or sporadic Alzheimer's disease patients and normal subjects was analyzed for presenilin-1 gene (Sherrington et al., Nature, Vol. 375, pp. 754–760, 1995), and the existence of various splicing variants has been reported (Clark et al,. Nature Genetics, Vol. 11, pp. 219–222, 1995; Anwar et al., Journal of Neurochemistry, Vol. 66, pp. 1774–1777, 1996).

Similar to presenilin-1 gene, presenelin-2 gene (Levy-Lahad et al., Genomics, Vol. 34, pp. 198–204, 1996; Levy-Lahad et al., Science, Vol. 269, pp. 973–977, 1995; Rogaev et al., Nature, Vol. 376, pp. 775–778, 1995) is composed of 12 exons, and 10 of these exons (exons 3–12) are known to code proteins. In addition, the existence of splicing variants lacking exon 8 as well as splicing variants simultaneously lacking exon 3 and exon 4 has been reported in normal human tissue (Prihar et al., NeuroReport, Vol. 7, pp. 1680–1684, 1996). However, there have been no splicing variants specific to Alzheimer's disease (and particularly sporadic Alzheimer's disease) reported for presenilin-2 gene.

An object of the present invention is to provide a novel method for screening and a novel method for identifying therapeutic agents for central nervous system diseases (such as Alzheimer's disease). In addition, an object of the present invention is to provide a novel method for examining central nervous system diseases (such as Alzheimer's disease). In addition, another object of the present invention is to provide a novel splicing variant originating in presenilin-2 that is useful in research on central nervous system diseases.

The present inventors found that expression of abnormal presenilin-2 mRNA splicing variants not found in the normal state ((i) splicing variant lacking exon 5, (ii) splicing variant lacking exon 3, and (iii) splicing variant lacking both exon 3 and exon 4 and retaining a portion of an intron sequence) is induced by exposure to oxidative stress or β-amyloid stimulation in the culture system of nerve cells. In addition, when the expression in human brain tissue was investigated for one of these splicing variants that is lacking exon 5, the present inventors made the unique discovery that this splicing variant lacking exon 5 is present at high frequency in the brain tissue of sporadic Alzheimer's disease patients, thereby leading to completion of the present invention.

DISCLOSURE OF THE INVENTION

Namely, the present invention is a method for screening therapeutic agents or preventive agents for central nervous system diseases, and a method for identifying the same, which comprises assaying the suppressing effect of a test substance on the expression of a splicing variant transcribed from presenilin-2 gene.

In addition, the present invention is a method for examining central nervous system diseases which comprises detecting the expression of a splicing variant transcribed from presenilin-2 gene in a test sample originated from an animal individual.

Moreover, the present invention is a nucleic acid having a base sequence originating in a splicing variant transcribed from presenilin-2 gene (in the following, referred to as a presenilin-2 splicing variant) and a polypeptide coded by said splicing variant.

BRIEF DESCRIPTION OF THE DRAWINGS

FIG. 3 is a drawing showing the cDNA sequence containing all exons of PS-2 (SEQ ID NO:1) PCR primer and the positions of each exon.

FIG. 4 is a drawing showing the sequence in the vicinity of the splicing site of a splicing variant lacking exon 3 and exon 4 of PS-2 (residues 297–806 of SEQ ID NO:4) and having a portion of an intron sequence.

FIG. 5 is an electrophoresis drawing (in which black and white colors have been reversed) showing the effect of a drug on induction of expression of PS-2 splicing variant in human nerve cells. In the drawing, N represents a control, H represents cells subjected to hypoxia, CHX represents cells subjected to hypoxia following addition of cycloheximide at 0.2 μg/ml or 1 μg/ml, DPI represents cells subjected to hypoxia following addition of diphenylene iodonium chloride at 5 μM or 20 μM, and NAC represents cells subjected to hypoxia following addition of N-acetyl-L-cysteine at 2 μM or 10 μM.

BEST MODE FOR CARRYING OUT THE INVENTION

Figure 1:
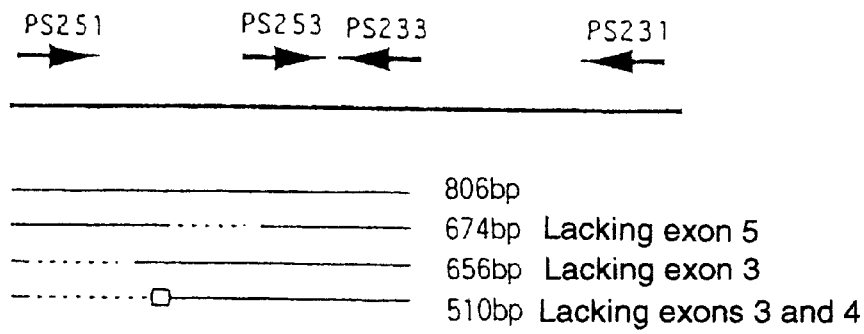
FIG. 1 is a schematic drawing showing a PCR primer of PS-2 gene and PCR products originating in various splicing variants.

In the present invention, a splicing variant lacking exon 5 refers to a splicing variant having a region in which exon 4 and exon 6 are joined. A splicing variant lacking exon 3 refers to a splicing variant having a region in which exon 2 and exon 4 are joined. A splicing variant lacking exon 3 and exon 4 while having a portion of an intron sequence refers to a splicing variant in which a sequence originating in an intron (intron located between exon 4 and exon 5) is added downstream from exon 2 and having an exon 5 region downstream from that.

SEQ.ID.NO: 1 of the Sequence Listing described later and FIG. 3 indicate the cDNA sequence (including all exons) of the previously reported human presenilin-2 gene. SEQ.ID.NOS: 2, 3 and 4 indicate cDNA sequences corresponding to human presenilin-2 splicing variants (mRNA) newly discovered by the present inventors. SEQ.ID.NO: 5 indicates the sequence of a mutant polypeptide coded by a splicing variant.

SEQ.ID.NO: 2 indicates the cDNA sequence of a splicing variant lacking exon 5 of human prenesilin-2 gene. The junction site of exon 4 and exon 6 in this splicing variant is located between bases 705th and 706th of SEQ.ID.NO: 2. The present inventors also discovered a splicing variant that is lacking exon 8 in addition to lacking exon 5, and the cDNA of such a splicing variant has a base sequence lacking bases 995th to 1093rd (region equivalent to exon 8) in SEQ.ID.NO: 2.

SEQ.ID.NO: 3 indicates a cDNA sequence of a splicing variant lacking exon 3 of human presenilin-2 gene. The junction site of exon 2 and exon 4 is located between bases 329th and 330th of SEQ.ID.NO: 3.

SEQ.ID.NO: 4 indicates the cDNA sequence of a splicing variant that is lacking exon 3 and exon 4 of human presenilin-2 gene while simultaneously having a portion of an intron sequence. The sequence originating in an intron (intron 4) present at the junction region of exon 2 and exon 5 exists from bases 330th to 409th of SEQ.ID.NO: 4.

SEQ.ID.NO: 5 indicates the base sequence (upper part of SEQ.ID.NO: 5) of the translation region of cDNA (SEQ.ID.NO: 2) of a splicing variant lacking exon 5 of human presenilin-2 gene, and the amino acid sequence (SEQ.ID.NO: 6) of a mutant polypeptide coded by the above base sequence.

As a result of performing homology searching on all sequences containied in known DNA databases (GenBank and EMBL) and protein databases (NBRF and SWISS-PROT) for the base sequences or amino acid sequences indicated in the above SEQ.ID.NOS: 2 through 6, there were no sequences that were completely identical, and these sequences are considered to be novel sequences.

The methods of the present invention (examination method, screening method and identification method) are applied to Alzheimer's disease (familial or sporadic) (Alzheimer's senile dementia) as well as other central nervous system diseases such as diffuse Levi's microsomia and boxer's brain, and are particularly preferably applied for Alzheimer's disease, and especially sporadic Alzheimer's disease. The methods of the present invention are applied to human diseases as well as diseases and disease models of other mammals such as monkeys, dogs, rats and mice.

The methods of screening and identification of the present invention are carried out by assaying the effect of suppressing expression of a splicing variant of presenilin-2. More specifically, screening or identification of a therapeutic agent or preventive agent of central nervous system diseases can be carried out by, for example, culturing cells or tissue in the presence of a test substance or administering a test substance into an animal individual, followed by detecting the expressed amount of presenilin-2 splicing variant in the cells or tissue.

In the case of performing screening or identification using a culture system, cells are cultured under conditions of, for example, exposure to oxidative stress (exposure to hypoxia, reoxygenation following exposure to hypoxia, addition of hydrogen peroxide, etc.) or β-amyloid stimulation. Since expression of abnormal presenilin-2 splicing variants like (i) through (iii) below, not observed in the normal state, are induced by culturing conditions like those described above, these culturing systems can be used as an in vitro pathological model to investigate the effects of the test substance.

(i) Expression of a splicing variant lacking exon 5 is induced by culturing cells with exposure to hypoxia. A variant further lacking exon 8 is also contained in the expressed splicing variant lacking exon 5.
(ii) Expression of a splicing variant lacking exon 3, and
(iii) expression of a splicing variant lacking exon 3 and exon 4 and having a portion of an intron sequence are induced by reoxygenation following exposure to hypoxia, by addition of hydrogen peroxide, and by β-amyloid stimulation.

In the case the amount of expression of abnormal splicing variants is decreased by the presence of a test substance in the culture system as compared with the absence of that test substance, that test substance is determined to have an effect that normalizes the pathological state.

The splicing variant of presenilin-2 that is lacking exon 5 has actually been specifically found in the brain tissue of Alzheimer's disease patients. Thus, a system that induces the splicing variant lacking exon 5, for example, a cell culture system that subjects cells to oxidative stress such as exposure to hypoxia, can be preferably used for screening or identifying therapeutic agents for Alzheimer's disease (and particularly sporadic Alzheimer's disease).

Central nervous system cells (nerve cells, glia cells, astrocytes, etc.) originating in mammals (humans, monkeys, etc.) as well as undifferentiated cells that can be induced into differentiating into nervous system cells and so forth can be used for the cells used in the culture system. The cells may be primary culture cells separated from animal tissue, or cancerated or immortalized cell lines. Examples of cell lines include human neuroblastoma SK-N-SH cells (ATCC HTB-11), human neuroblastoma IMR-32 cells (ATCC CCL-127), human neuroblastoma SKN-MC cells (ATCC HTB-10), and human kidney transformed cells 293 (ATCC CRL-1573).

Exposure to hypoxia (hypoxic treatment) can be performed by, for example, culturing cells for at least about 48 hours under normal oxygen conditions (about 20% $O_2$ and about 5% $CO_2$), transferring to an incubator under low oxygen conditions ($O_2$ concentration: 1% or less, about 95% $N_2$ and about 5% $CO_2$) and culturing for about 12–48 hours. Reoxygenation can be performed by returning to normal culture conditions and culturing the cells after subjected to hypoxic treatment as the above (Japanese Laid-Open Patent Publication No. 9-238685; Ogawa et al., Journal of Clinical Investigation, Vol. 85, pp. 1090–1098, 1996). Hydrogen peroxide addition can be performed by adding hydrogen peroxide to the medium to a final concentration of 44–440 $\mu$M and culturing for about 2 hours. In addition, β-amyloid stimulation can be performed by adding β-amyloid protein or its partial peptide (for example, $A\beta_{25-35}$ (partial peptide consisting of the 25th to 35th amino acid residues of β-amyloid protein) to a concentration of 0.5–5 $\mu$M, and culturing for about 16 hours.

An abnormal splicing variant of presenilin-2 can also be used for examination of central nervous system diseases. The examination method of the present invention can be carried out by detecting the expression of a splicing variant of presenilin-2 in a test sample originated from an animal individual. More specifically, for example, a splicing variant of presenilin-2 in RNA extracted from a test sample may be detected. Alternatively, a mutant polypeptide, which is originated from a splicing variant, in a test sample may be detected.

In Alzheimer's disease patients (and particularly sporadic Alzheimer's disease patients), a splicing variant lacking exon 5 of presenilin-2 is found in brain tissue at a frequency that is clearly higher than that in normal individuals. Thus, in the case a splicing variant lacking exon 5 of presenilin-2 is detected, that patient can be determined to have a high risk for Alzheimer's disease.

Examples of test samples include tissue and humor originated from an animal individual. Particularly preferable examples of body tissue include brain tissue including the central nervous system (such as nerve cells, glia cells and astrocytes) and fibroblasts. Examples of humor include serum and plasma.

In the methods of the present invention, in order to detect expression of a splicing variant of presenilin-2, RNA (mRNA) may be extracted from cells or tissue, and a splicing variant of presenilin-2 in that RNA may be detected. Alternatively, expression of a splicing variant may be detected indirectly by detecting mutant polypeptide coded by the splicing variant.

Presenilin-2 gene has previously been cloned from humans, rats, mice and so forth, and its base sequence and amino acid sequence have been determined ((Human) GeneBank/EMBL Accession No. L43964 and No. U50871, SWISS-PROT Accession No. P49810; Genomics, Vol. 34, pp. 198–204, 1996; Science, Vol. 269, pp. 973–977, 1995; Nature, Vol. 376, pp. 775–778, 1995: (Rat) Gene, Vol. 197, pp. 383–387, 1997; GeneBank/EMBL Accession No. D83700: (Mouse) GeneBank/EMBL Accession No. AF038935). Thus, this sequence information can be used for detection of a splicing variant. In addition, information on the base sequences of each of the splicing variants of human origin shown in the Sequence Listing described later can also be used.

In the case of detecting a splicing variant in RNA, RNA (mRNA) is prepared from cells or tissue, and the junction site along with the regions before and after them resulting from abnormal splicing are detected using that mRNA or cDNA prepared from that mRNA. An ordinary polymerase chain reaction (PCR) method, RNAase protection assay method or Northern blot analysis can be used for detection. By the use of these methods, fragments resulting from abnormal splicing are detected based on fragment size.

In the case of using the PCR method ("PCR Protocols", Innis M A, Gelfad D H, Sninsky J J and White T J, eds., Academic Press, San Diego, 1990), suitable primers (sense primer and anti-sense primer) are designed and synthesized in order to amplify the fragment including the junction site along with the regions before and after them resulting from abnormal splicing. By using these primers and using cDNA synthesized from mRNA as the template to perform PCR and isolating the resulting PCR products by electrophoresis and so forth as necessary, a splicing variant can be detected by investigating the fragment size. In addition, the base sequences of the PCR products can be determined to identify the splicing variant in detail.

The RNAase protection assay method (Nucleic Acid Research, Vol. 12, pp. 7035–7056, 1984) uses RNAase having the property of specifically decomposing single-strand RNA but not decomposing double-strand RNA, and the anti-sense strand RNA for the RNA to be examined is normally used as a probe. After hybridizing the RNA to be examined and the labeled RNA probe, the RNAase is allowed to act to decompose the non-hybridized RNA. This is then separated by electrophoresis and so forth to detect and quantify the fragments. Preparation of the RNA probe is performed by, for example, amplifying a suitable region desired to be used as a probe by PCR and so forth using cDNA synthesized from mRNA as the template, and connecting the resulting fragment in a suitable direction downstream from a promoter in a plasmid vector to construct a vector for RNA probe synthesis. This vector can be used with RNA polymerase such as T3, T7, SP6 or others to produce the RNA probe in vitro. In the case of detecting a splicing variant of presenilin-2, the region used for the probe is a region that contains the junction site at which abnormal splicing occurs. For example, the region that includes the region from exon 4 to exon 6 can be selected.

In addition to the methods described above, junction sites that are newly formed as a result of abnormal splicing can be detected directly using a nucleic acid probe. In this case, DNA (oligonucleotide) complementary to a region that contains the junction site and the regions on both sides is designed and synthesized based on sequence information of the junction site to be detected and its surrounding sequences, and this labeled DNA is then used as a probe. Using the above probe, northern blot analysis or southern blot analysis and so forth is performed on mRNA or its cDNA obtained from test cells or tissue, or on a DNA fragment amplified by PCR by using these as templates, after which a judgment is made as to whether or not nucleic acid that hybridizes with the probe is present.

In the case of detecting a splicing variant indirectly by detecting a mutant polypeptide, a method can be used in which, for example, detection is made immunochemically using an antibody that specifically recognizes the mutant polypeptide. An antibody that reacts with the mutant polypeptide but does not cross-react with normal presenilin-2 can be used as the specific antibody. An antigen, for example, prepared from the mutant polypeptide using gene recombination technology can be used for the antigen for preparing the antibody. Alternatively, a synthetic peptide may be used for the antigen. For example, in the case of desiring to detect a mutant polypeptide coded by a splicing variant lacking exon 5, a specific antibody can be prepared by using as an antigen a synthetic peptide and so forth of a suitable length that contains the sequence of 6 amino acids on the C-terminal side of SEQ.ID.NO: 5.

Mutant polypeptide or normal presenilin-2 can be prepared using a recombinant expression vector in which cDNA to a splicing variant or normal mRNA of presenilin-2 gene is linked to a suitable vector plasmid.

cDNA of presenilin-2 gene can be isolated and obtained, for example, by using as gene sources the cDNA of mRNA prepared from animal tissue or cells (such as central nervous system cells). In the case of obtaining cDNA of a splicing variant, cells can be used that have been cultured under conditions such as the above oxidative stress (exposure to hypoxia, subjecting to reoxygenation following exposure to hypoxia, addition of hydrogen peroxide, etc.) or β-amyloid stimulation. cDNA fragments are obtained from these gene sources by PCR using a primer designed on the basis of known sequence information. Desired cDNA can also be obtained by colony hybridization or plaque hybridization and so forth by using as probes fragments amplified by PCR or synthetic oligonucleotides and using a cDNA library prepared from the gene sources or a commercially available library as necessary.

Examples of expression systems (host-vector systems) for producing presenilin-2 or its mutant polypeptide include expression systems such as mammalian cells, insect cells, yeast and bacteria. In order to obtain functional protein, it is preferable to use insect cells (Spodoptera frugiperda SF9, SF21, etc.) and mammalian cells (monkey COS-7 cells, Chinese hamster CHO cells, human HeLa cells, etc.) as hosts. An example of a vector in the case of using insect cells for the host is Baculovirus vector. Examples of vectors in the case of using mammalian cells for the host include retrovirus vector, papilloma virus vector, vaccinia virus vector and SV40 vector. Expression vectors can be constructed by inserting cDNA into downstream of a suitable promoter in these vectors.

The desired polypeptide is produced by transforming host cells with the resulting expression vector, and culturing the transformant in a suitable medium. Polypeptide produced in the host cells can be harvested by crushing the cells by a physical technique using a frictional crushing device such as a Dyno Mill or by a chemical technique such as lysozyme treatment, and isolating from the resulting cell extract by known purification methods (such as salting out method using inorganic salts, fractional precipitation by organic solvent, adsorption/desorption methods using ion exchange resin or various types of column chromatography, gel filtration and methods using protein precipitant) or a suitable combination thereof.

An example of cDNA used for the DNA that codes for presenilin-2 or its mutant polypeptide is cDNA of human origin having the base sequences shown in SEQ.ID.NOS: 1–4 of the Sequence Listing. In addition, genes and their alleles originated from other species that exist in nature may also be used. In addition, base sequences are not limited to those existing in nature, but rather DNA corresponding to the amino acid sequence of a polypeptide can also be designed and used. In this case, there are one to six types of the codon that codes each amino acid. The codon to be used may be selected arbitrarily, and a sequence having the highest expression efficiency can be designed in consideration of the codon usage frequency and so forth of the host being used.

In addition, a portion of the amino acid sequence of the mutant polypeptide originated from a splicing variant may be modified or altered provided the modification or alteration is to a degree to which the mutant polypeptide still substantially retains the equivalent immunogenicity or function. For example, an example of a polypeptide originated from a splicing variant lacking exon 5 of human presenilin is that having the amino acid sequence shown in SEQ.ID.NO: 5, and other examples include those having sequences in which one or a plurality of amino acids are added, deleted or substituted in that amino acid sequence. The number of amino acids that are added, deleted or substituted is normally from 1 to about 20, preferably from 1 to about 10, and more preferably from 1 to about 5. In this polypeptide, the homology of the amino acid sequence with the amino acid sequence shown in SEQ.ID.NO: 5 is usually at least 80%, preferably at least 90%, and more preferably at least 95%.

DNA that codes the designed amino acid sequence can be obtained by DNA chemical synthesis, fragmentation and coupling of the above cDNA or partial alteration of the base sequence and so forth. Partial alteration and mutation introduction of an artificial base sequence can be performed by site-specific mutagenesis using a primer comprising synthetic oligonucleotide that codes for the desired alteration (Mark, D. F. et al., Proceedings of National Academy of Sciences, Vol. 81, pp. 5662–5666 (1984)).

In addition, abnormal splicing variants of presenilin-2 (particularly a splicing variant lacking exon 5) along with its detection method are useful in pathological research on central nervous system diseases (particularly Alzheimer's disease). In-depth analysis of function in cells after inserting a recombinant expression plasmid containing cDNA of an abnormal splicing variant into those cells, and analysis of the function and action of a mutant polypeptide originated from a splicing variant are considered to lead to elucidation of the mechanism of pathogenesis.

Although the following provides a more detailed explanation of the present invention through its Examples, these Examples do not limit the present invention.

Furthermore, in the following Examples, unless clearly indicated otherwise, each procedure was performed according to the methods described in "Molecular Cloning" (Sambrook, J., Fritsch, E. F. and Maniatis, T. eds., published in 1989 by Cold Spring Harbor Laboratory Press), or in the case of using commercially available reagents or kits, such reagents or kits were used according to the instructions provided with the commercially available products.

EXAMPLES

Example 1

Detection of Splicing Variants in Human Nerve Cells (1) Culturing of Human Nerve Cells and Preparation of RNA After culturing human neuroblastoma SK-N-SH cells (ATCC HTB-11) in α-MEM medium (α-Minimum Essential Medium; available from GIBCO CO.) containing 10% fetal bovine serum in a 10 cm diameter culture plates at 37° C. for about 48 hours in a $CO_2$ incubator to a confluent state, the medium was replaced with the same medium not containing fetal bovine serum followed by additional culturing for about 2 hours.

The above cultured cells were additionally cultured under the conditions (i) to (iv) indicated below (culturing was continued for an additional 16 hours under the same conditions as above for the control).

(i) Hypoxic treatment: The culture plate was transferred to a low oxygen incubator (oxygen concentration: 1% or less, 95% $N_2$, 5% $CO_2$) (available from Coy Laboratory Products Co.) and incubated for 16 hours.

(ii) Reoxgenation treatment: After transferring the culture plate to a low oxygen incubator (oxygen concentration: 1% or less, 95% $N_2$, 5% $CO_2$) and incubating for 16 hours, the cell plate was returned to an ordinary $CO_2$ incubator (oxygen concentration: 20%, 75% $N_2$, 5% $CO_2$) and incubated for 4 hours.

(iii) β-amyloid stimulation: $Aβ_{25-35}$ (available from Sigma Co.) was added to the medium to a final concentration of 0.5 μM or 5 μM followed by incubating for 16 hours.

(iv) Hydrogen peroxide ($H_2O_2$) addition: Hydrogen peroxide ($H_2O_2$) was added to the medium to a final concentration of 44 μM or 440 μM followed by incubating for 2 hours.

Each of the cells cultured in the manner described above were collected and washed with phosphate buffered saline (PBS). After suspending the cells in 700 μl of cell lysing buffer (RLT solution, available from QIAGEN Co.), the cells were crushed to obtain a cell extract. Total RNA was then prepared from this cell extract. Preparation of RNA was performed using an RNA preparation kit (trade name: Rneasy Total RNA Kit, available from QIAGEN Co.).

(2) Detection of Splicing Variants

Using, the RNA (total RNA, 1 μg) obtained in section (1) above as template, this RNA was allowed to react for 1 hour at 42° C. in 0.05 ml of a buffer (0.05 M Tris-HCl, pH 8.3, 0.075 MN KCl, 0.003 M $MgCl_2$, DTT and 0.0002 M deoxynucleotides) containing oligo dT primer (50 pmole), random oligonucleotide (5 pmole) and reverse transcriptase (available from Promega Co., Moloney leukaemia virus reverse transcriptase) (200 units) to synthesize single-strand cDNA. Using the resulting single-strand cDNA, splicing variants were detected by polymerase chain reaction (PCR) in the manner described below.

Four types of PCR primers consisting of PS251 (SEQ.ID.NO: 7) (sense primer), PS253 (SEQ.ID.NO: 8) (sense primer), PS233 (SEQ.ID.NO: 9) (anti-sense primer) and PS231 (SEQ.ID.NO: 10) (anti-sense primer) were used for the PCR primers for presenilin-2 (PS-2) gene.

The location and direction on PS-2 gene corresponding to each primer are shown in FIG. 1 and FIG. 3.

The first round of PCR reaction was performed using the single-strand cDNA obtained above as the template, and using PS251 (SEQ.ID.NO: 7) (sense primer) and PS231 (SEQ.ID.NO: 10) (anti-sense primer) as the primers for amplifying the entire coding region (about 1.6 kbp) of PS-2 gene. PCR was performed under conditions of 95° C. for about 40 seconds for the denaturing reaction, 72° C. for 1 minute for elongation reaction, and 60° C. for about 30 seconds for annealing (number of cycles: 30 cycles).

The second round of PCR was performed after diluting the reaction mixture 1:5 and using 1 μl of that diluted liquid as template. PS251 (SEQ.ID.NO: 7) (sense primer) and PS233 (SEQ.ID.NO: 9) (anti-sense primer) were used as PCR primers for detecting 5'-terminal fragments of the coding region of PS-2, while PS253 (SEQ.ID.NO: 8) (sense primer) and PS231 (SEQ.ID.NO: 10) (anti-sense primer) were used as PCR primers for detecting 3'-terminal fragments. PCR was performed under the same conditions as described above. The sizes of the DNA fragments were investigated by performing polyacrylamide gel electrophoresis on the resulting PCR products.

Figure 2:
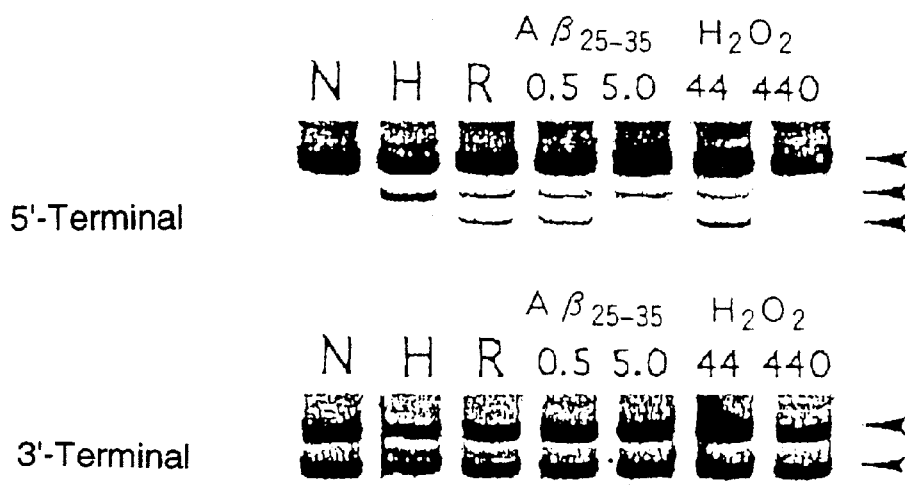
FIG. 2 is an electrophoresis drawing (in which black and white colors have been reversed) showing induction of expression of PS-2 splicing variant in human nerve cells. In the drawing, N represents a control, H represents cells subjected to hypoxia, R represents cells subjected to reoxygenation following exposure to hypoxia, $A\beta_{25\text{-}35}$ represents cells cultured with the addition at 0.5 µM or 5 µM of $A\beta_{25\text{-}35}$ (partial peptide consisting of the 25th to 35th amino acid residues of β-amyloid protein), while $H_2O_2$ represents cells to which were added 44 µM or 440 µM hydrogen peroxide.

Those results are shown in FIG. 2. As shown in FIG. 2, as a result of performing PCR in which the 5'-terminal fragment was amplified, a single band not observed in the control was detected in the sample originated from cells subjected to hypoxic treatment. In addition, two bands each not observed in the control were detected in the samples originated from cells subjected to reoxygenation following exposure to hypoxia and in the cells stimulated with β-amyloid, while three bands not observed in the control were observed in the sample originated from cells cultured following addition of hydrogen peroxide. In contrast, as a result of performing PCR in which the 3'-terminal fragment was amplified, two major bands each were similarly confirmed in all of the samples, including the control.

On the basis of these results, it was considered that a 5'-terminal splicing abnormality occurred due to hypoxic treatment, and at least one type of splicing variant was induced. In addition, it was considered that a 5'-terminal splicing abnormality also occurred due to reoxygenation following exposure to hypoxia and due to β-amyloid stimulation, and two types and three types, respectively, of splicing variants were induced.

(3) Analysis of PS-2 Splicing Variants

The base sequences of the PS-2 splicing variants found in section (2) above were determined in the manner described below. Agarose gel electrophoresis was performed on the PCR products in the same manner as in section (2) above, and DNA fragments thought to be originated from splicing variants (5 types for the 5'-terminal fragments and 3 types for the 3'-terminal fragments) were collected from the gel followed by coupling each to vector plasmid pGEM-T (available from Promega Co.). The base sequences of the inserted fragment portions were determined by the dideoxy method using the resulting recombinant plasmids. Base sequences were determined using an automated sequencer (373A DNA Sequencing System) (available from Applied Biosystems Co.).

Those splicing variants confirmed as a result of determining the base sequences are schematically illustrated in FIG. 1.

Of the two types of fragments found on the 3'-terminal, one was a normal splicing product, and the other was a splicing variant lacking exon 8. The existence of a splicing variant lacking exon 8 in normal tissue has been previously reported, and this deletion is considered not to have an effect on the function of PS-2 protein.

On the other hand, the splicing variant found in the 5'-terminal fragment following hypoxic treatment was determined to be a splicing variant lacking exon 5. A splicing variant lacking exon 5 has never been previously reported in normal tissue. The cDNA base sequence corresponding to this splicing variant (lacking exon 5) is shown in SEQ.ID.NO: 2 of the Sequence Listing. The junction site of exon 4 and exon 6 in this splicing variant is located between bases 705th and 706th of SEQ.ID.NO: 2. A frame shift occurs downstream from this junction site due to deletion of exon 5 resulting in the presence of an open reading frame at bases 350th–724th. The base sequence of this open reading frame along with the amino acid sequence of the mutant polypeptide (124 amino acid residues) coded here are shown in SEQ.ID.NO: 5–6. The mutant polypeptide has a sequence in which additional five amino acid residues resulted from the frame shift are added to the C-terminal portion of the 119 amino acid residues N-terminal portion of normal presenilin-2 protein (448 amino acid residues).

In addition, a splicing variant also lacking exon 8 was also present among the splicing variants lacking exon 5, and the cDNA of this splicing variant has a base sequence in which bases 995th–1093rd (region equivalent to exon 8) is lacking in SEQ.ID.NO: 2.

One of the splicing variants found in the 5'-terminal fragments following reoxygenation after exposure to hypoxia, β-amyloid stimulation and addition of hydrogen peroxide was a splicing variant lacking exon 3, while another was a splicing variant which, in addition to lacking exon 3 and exon 4, was spliced inside of intron 4 (intron between exon 4 and exon 5).

The cDNA sequence of the splicing variant lacking exon 3 is shown in SEQ.ID.NO: 3. The junction site of exon 2 and exon 5 is located between bases 329th and 330th of SEQ.ID.NO: 3.

In addition, the cDNA sequence of the splicing variant lacking exons 3 and 4 and having a portion of an intron sequence is shown in SEQ.ID.NO: 4 and FIG. 4. The sequence derived from the intron (intron 4) present at the junction region of exon 2 and exon 5 is at bases 330th–409th of SEQ.ID.NO: 4.

Although a splicing variant simultaneously lacking exon 3 and exon 4 has been previously reported in normal tissue, a variant lacking only exon 3 as well as a splicing variant lacking exons 3 and 4 while also having a portion of an intron sequence have not been reported in the past.

Example 2
Effect of Drug on Induction of the Expression of PS-2 Splicing Variants in Human Nerve Cells
(1) Culturing of Human Nerve Cells Under Hypoxic Conditions and Preparation of RNA Human neuroblastoma SK-N-SH cells were cultured under hypoxic conditions as indicated below in compliance with section (1) of the above Example 1. Namely, after culturing in α-MEM medium containing 10% fetal bovine serum in a $CO_2$ incubator (oxygen concentration: 20%) at 37° C. to a confluent state (about 48 hours), the medium was replaced with the same medium not containing fetal bovine serum. Cycloheximide (final concentration: 0.2 µg/ml or 1 µg/ml), N-acetyl-L-cysteine (final concentration: 2 µM or 10 µM) or diphenylene iodonium chloride (final concentration: 5 µM or 20 µM) was added to the medium. The culture was then transferred to a low oxygen incubator (oxygen concentration: 1% or less) and cultured for an additional 16 hours.

Each of the cells cultured in the manner described above were collected and RNA (total RNA) was prepared from the cells according to the same method as section (1) of the above Example 1.

(2) Detection of PS-2 Splicing Variants

Detection of PS-2 splicing variants was performed according to the same method as in section (2) of the above Example 1 using the RNA (total RNA) obtained in section (1) above. Namely, single-strand cDNA was prepared using the above RNA as template, and a first round of PCR was performed using the resulting cDNA as template to amplify the DNA fragment containing the entire length of the PS-2 coding region. PS251 (SEQ.ID.NO: 7) (sense primer) and PS231 (SEQ.ID.NO: 10) (anti-sense primer) were used as PCR primers.

After diluting the reaction liquid and using 1 µl thereof as template, a second round of PCR was performed to amplify the DNA fragment containing the 5'-terminal of the PS-2 coding region. PS251 (SEQ.ID.NO: 7) (sense primer) and PS233 (SEQ.ID.NO: 9) (anti-sense primer) were used as PCR primers. Polyacrylamide gel electrophoresis was performed on the resulting PCR product to investigate the presence or absence of fragments derived from splicing variants (such as a fragment having a length of about 640 bases originated from a splicing variant lacking exon 5).

Those results are shown in FIG. 5. As shown in FIG. 5, expression of a splicing variant lacking exon 5 induced by hypoxic treatment was inhibited by treatment with cycloheximide, a protein synthesis inhibitor. On the basis of this finding, it was considered that protein newly produced during hypoxic treatment is involved in induction of expression of a splicing variant lacking exon 5. In addition, expression of a splicing variant lacking exon 5 was also inhibited by the antioxidants, N-acetyl-L-cysteine or diphenylene iodonium chloride. On the basis of these findings, it was considered that some form of oxidative stress in a hypoxic state, such as active oxygen, is involved in. the expression of PS-2 splicing variant lacking exon 5 that is induced by hypoxic treatment.

Example 3
Expression of PS-2 Splicing Variants in Human Brain Tissue

Detection of PS-2 splicing variant lacking exon 5 was performed for samples of human brain tissue. Human brain tissue samples consisted of a total of 47 samples collected from brains of sporadic AD patients (30 cases) and normal brain subjects (17 cases) of nearly the same age.

After homogenizing the brain tissue test samples (frozen storage samples), RNA was prepared from the resulting extract in the same manner as section (1) of the above Example 1. Detection of PS-2 splicing variants was performed using PCR in the same manner as section (2) of Example 1 and section (2) of Example 2 using the resulting RNA.

Those results are shown in Table 1. A splicing variant lacking exon 5 was expressed in 3 of 17 normal brains (17%). In contrast, this splicing variant was expressed in 21 of 30 brains of sporadic AD patients (70%). Thus, it was determined that a splicing variant lacking exon 5 is expressed at a clearly higher frequency in the brains of sporadic AD patients than in normal brains.

TABLE 1

| No. | Case | Age | Presence or absence of PS-2 splicing variant |
|-----|------|-----|---------|
| N1  | N    | 81  | −       |
| N2  | N    | 80  | −       |
| N3  | N    | 80  | −       |
| N4  | N    | 75  | −       |
| N5  | N    | 91  | +       |
| N6  | N    | 79  | −       |
| N7  | N    | 93  | −       |
| N8  | N    | 89  | −       |
| N9  | N    | 81  | −       |
| N10 | N    | 84  | +       |
| N11 | N    | 92  | −       |
| N12 | N    | 92  | −       |
| N13 | N    | 92  | −       |
| N14 | N    | 88  | −       |
| N15 | N    | 86  | −       |
| N16 | N    | 84  | +       |
| N17 | N    | 85  | −       |
| A1  | AD   | 68  | +       |
| A2  | AD   | 91  | +       |
| A3  | AD   | 80  | +       |
| A4  | AD   | 82  | +       |
| A5  | AD   | 78  | +       |
| A6  | AD   | 87  | −       |
| A7  | AD   | 79  | +       |
| A8  | AD   | 62  | +       |
| A9  | AD   | 71  | −       |
| A10 | AD   | 84  | +       |
| A11 | AD   | 88  | +       |
| A12 | AD   | 81  | +       |
| A13 | AD   | 74  | −       |
| A14 | AD   | 75  | −       |
| A15 | AD   | 63  | +       |
| A16 | AD   | 74  | +       |
| A17 | AD   | 64  | +       |
| A18 | AD   | 86  | +       |
| A19 | AD   | 69  | −       |
| A20 | AD   | 82  | +       |
| A21 | AD   | 91  | −       |
| A22 | AD   | 91  | +       |

TABLE 1-continued

| No. | Case | Age | Presence or absence of PS-2 splicing variant |
|---|---|---|---|
| A23 | AD | 97 | + |
| A24 | AD | 89 | + |
| A25 | AD | 70 | + |
| A26 | AD | 75 | + |
| A27 | AD | 69 | − |
| A28 | AD | 77 | − |
| A29 | AD | 83 | + |
| A30 | AD | 81 | − |

AD: Sporadic Alzheimer's disease
N: Normal

Industrial Applicability

According to the method of the present invention, screening and identification of therapeutic agents or preventive agents for central nervous system diseases such as sporadic Alzheimer's disease, which had been difficult in the past, can be carried out efficiently. Since the point of action of drugs discovered or identified by the screening method of the present invention is clearly determined, they are advantageous for development as pharmaceuticals.

In addition, diagnosis of central nervous system diseases, particularly sporadic Alzheimer's disease for which diagnosis was difficult in the past, can be carried out preferably.

In addition, abnormal splicing variants of presenilin-2 and method for detecting thereof are useful in pathological research on central nervous system diseases (particularly Alzheimer's disease) as well. In-depth analysis of the intracellular function of abnormal splicing variants, and analysis of the function and action of mutant polypeptides originated from splicing variants, lead to elucidation of the mechanism of pathogenesis.

What is claimed is:

1. A method for examining a central nervous system disease which comprises detecting, in a test sample originated from an animal individual, an expression of a presenilin-2 splicing variant lacking exon 5, wherein said central nervous system diseases is Alzheimer's disease.

2. The method according to claim 1 wherein the detection of an expression of a presenilin-2 splicing variant lacking exon 5 is carried out by (1) detecting a nucleic acid which is identical or complementary to a presenilin-2 splicing variant lacking exon 5; or (2) detecting a mutant polypeptide originated from a presenilin-2 splicing variant lacking exon 5.

3. The method according to claim 1 wherein the detection of an expression of a presenilin-2 splicing variant lacking exon 5 is carried out by detecting a nucleic acid, said nucleic acid being selected from the group consisting of (1) a DNA containing at least the $705^{th}$ and $706^{th}$ bases in the base sequence described in SEQ ID NO:2 or a complement thereof; and (2) a RNA corresponding to the DNA of (1).

4. The method according to claim 1 wherein the detection of an expression of a presenilin-2 splicing variant lacking exon 5 is carried out by detecting a nucleic acid, said nucleic acid being selected from the group consisting of (1) a DNA having a base sequence described in SEQ ID NO:2 or a complement thereof;

(2) a DNA having a base sequence lacking the $995^{th}$ to $1093^{rd}$ bases in SEQ ID NO:2 or a complement thereof; and (3) a RNA corresponding to the DNA of (1) or (2).

5. The method according to claim 1 wherein the detection of an expression of a presenilin-2 splicing variant lacking exon 5 is carried out by detecting a nucleic acid, said nucleic acid coding for a mutant polypeptide selected from the group consisting of (1) a polypeptide having an amino acid sequence described in SEQ ID NO:6; and (2) a polypeptide having at least 80% sequence homology with the polypeptide of (1).

6. The method according to claim 1 wherein the detection of an expression of a presenilin-2 splicing variant lacking exon 5 is carried out by detecting a mutant polypeptide, said polypeptide being selected from the group consisting of (1) a polypeptide having an amino acid sequence described in SEQ ID NO:6; and (2) a polypeptide having at least 80% sequence homology with the polypeptide of (1).

7. The method according to any one of claims 1 to 6 wherein the animal individual is a human.

* * * * *

SEQUENCE LISTING

<160> NUMBER OF SEQ ID NOS: 10

<210> SEQ ID NO 1
<211> LENGTH: 2144
<212> TYPE: DNA
<213> ORGANISM: Homo sapiens
<220> FEATURE:
<221> NAME/KEY: CDS
<222> LOCATION: (350)..(1696)
<223> OTHER INFORMATION:

<400> SEQUENCE: 1

```
gcatttccag cagtgaggag acagccagaa gcaagctatt ggagctgaag gaacctgaga      60
cagaagctag tcccccctct gaattttact gatgaagaaa ctgaggccac agagctaaag     120
tgacttttcc caaggtcgcc cagcgaggac gtgggacttc tcagacgtca ggagagtgat     180
gtgagggagc tgtgtgacca tagaaagtga cgtgttaaaa accagcgctg ccctctttga     240
aagccaggga gcatcattca tttagcctgc tgagaagaag aaaccaagtg tccgggattc     300
agacctctct gcggccccaa gtgttcgtgg tgcttccaga ggcagggct atg ctc aca    358
                                                       Met Leu Thr
                                                         1 ttc atg gcc tct gac agc gag gaa gaa gtg tgt gat gag cgg acg tcc     406
Phe Met Ala Ser Asp Ser Glu Glu Glu Val Cys Asp Glu Arg Thr Ser
     5                  10                  15 cta atg tcg gcc gag agc ccc acg ccg cgc tcc tgc cag gag ggc agg     454
Leu Met Ser Ala Glu Ser Pro Thr Pro Arg Ser Cys Gln Glu Gly Arg
 20                  25                  30                  35 cag ggc cca gag gat gga gag aac act gcc cag tgg aga agc cag gag     502
Gln Gly Pro Glu Asp Gly Glu Asn Thr Ala Gln Trp Arg Ser Gln Glu
                 40                  45                  50 aac gag gag gac ggt gag gag gac cct gac cgc tat gtc tgt agt ggg     550
Asn Glu Glu Asp Gly Glu Glu Asp Pro Asp Arg Tyr Val Cys Ser Gly
             55                  60                  65 gtt ccc ggg cgg ccg cca ggc ctg gag gaa gag ctg acc ctc aaa tac     598
Val Pro Gly Arg Pro Pro Gly Leu Glu Glu Glu Leu Thr Leu Lys Tyr
```

-continued

|     |     |     |     | 70  |     |     |     | 75  |     |     |     | 80  |     |     |     |      |
|---|---|---|---|---|---|---|---|---|---|---|---|---|---|---|---|---|
| gga | gcg | aag | cac | gtg | atc | atg | ctg | ttt | gtg | cct | gtc | act | ctg | tgc | atg | 646 |
| Gly | Ala | Lys | His | Val | Ile | Met | Leu | Phe | Val | Pro | Val | Thr | Leu | Cys | Met |     |
|     |     | 85  |     |     |     | 90  |     |     |     | 95  |     |     |     |     |     |     |
| atc | gtg | gtg | gta | gcc | acc | atc | aag | tct | gtg | cgc | ttc | tac | aca | gag | aag | 694 |
| Ile | Val | Val | Val | Ala | Thr | Ile | Lys | Ser | Val | Arg | Phe | Tyr | Thr | Glu | Lys |     |
| 100 |     |     |     |     | 105 |     |     |     |     | 110 |     |     |     |     | 115 |     |
| aat | gga | cag | ctc | atc | tac | acg | aca | ttc | act | gag | gac | aca | ccc | tcg | gtg | 742 |
| Asn | Gly | Gln | Leu | Ile | Tyr | Thr | Thr | Phe | Thr | Glu | Asp | Thr | Pro | Ser | Val |     |
|     |     |     | 120 |     |     |     |     | 125 |     |     |     |     | 130 |     |     |     |
| ggc | cag | cgc | ctc | ctc | aac | tcc | gtg | ctg | aac | acc | ctc | atc | atg | atc | agc | 790 |
| Gly | Gln | Arg | Leu | Leu | Asn | Ser | Val | Leu | Asn | Thr | Leu | Ile | Met | Ile | Ser |     |
|     |     |     | 135 |     |     |     |     | 140 |     |     |     |     | 145 |     |     |     |
| gtc | atc | gtg | gtt | atg | acc | atc | ttc | ttg | gtg | gtg | ctc | tac | aag | tac | cgc | 838 |
| Val | Ile | Val | Val | Met | Thr | Ile | Phe | Leu | Val | Val | Leu | Tyr | Lys | Tyr | Arg |     |
|     |     | 150 |     |     |     |     | 155 |     |     |     |     | 160 |     |     |     |     |
| tgc | tac | aag | ttc | atc | cat | ggc | tgg | ttg | atc | atg | tct | tca | ctg | atg | ctg | 886 |
| Cys | Tyr | Lys | Phe | Ile | His | Gly | Trp | Leu | Ile | Met | Ser | Ser | Leu | Met | Leu |     |
|     | 165 |     |     |     |     | 170 |     |     |     |     | 175 |     |     |     |     |     |
| ctg | ttc | ctc | ttc | acc | tat | atc | tac | ctt | ggg | gaa | gtg | ctc | aag | acc | tac | 934 |
| Leu | Phe | Leu | Phe | Thr | Tyr | Ile | Tyr | Leu | Gly | Glu | Val | Leu | Lys | Thr | Tyr |     |
| 180 |     |     |     |     | 185 |     |     |     |     | 190 |     |     |     |     | 195 |     |
| aat | gtg | gcc | atg | gac | tac | ccc | acc | ctc | ttg | ctg | act | gtc | tgg | aac | ttc | 982 |
| Asn | Val | Ala | Met | Asp | Tyr | Pro | Thr | Leu | Leu | Leu | Thr | Val | Trp | Asn | Phe |     |
|     |     |     | 200 |     |     |     |     | 205 |     |     |     |     | 210 |     |     |     |
| ggg | gca | gtg | ggc | atg | gtg | tgc | atc | cac | tgg | aag | ggc | cct | ctg | gtg | ctg | 1030 |
| Gly | Ala | Val | Gly | Met | Val | Cys | Ile | His | Trp | Lys | Gly | Pro | Leu | Val | Leu |     |
|     |     |     | 215 |     |     |     |     | 220 |     |     |     |     | 225 |     |     |     |
| cag | cag | gcc | tac | ctc | atc | atg | atc | agt | gcg | ctc | atg | gcc | cta | gtg | ttc | 1078 |
| Gln | Gln | Ala | Tyr | Leu | Ile | Met | Ile | Ser | Ala | Leu | Met | Ala | Leu | Val | Phe |     |
|     |     |     | 230 |     |     |     |     | 235 |     |     |     |     | 240 |     |     |     |
| atc | aag | tac | ctc | cca | gag | tgg | tcc | gcg | tgg | gtc | atc | ctg | ggc | gcc | atc | 1126 |
| Ile | Lys | Tyr | Leu | Pro | Glu | Trp | Ser | Ala | Trp | Val | Ile | Leu | Gly | Ala | Ile |     |
|     | 245 |     |     |     |     | 250 |     |     |     |     | 255 |     |     |     |     |     |
| tct | gtg | tat | gat | ctc | gtg | gct | gtg | ctg | tgt | ccc | aaa | ggg | cct | ctg | aga | 1174 |
| Ser | Val | Tyr | Asp | Leu | Val | Ala | Val | Leu | Cys | Pro | Lys | Gly | Pro | Leu | Arg |     |
| 260 |     |     |     |     | 265 |     |     |     |     | 270 |     |     |     |     | 275 |     |
| atg | ctg | gta | gaa | act | gcc | cag | gag | aga | aat | gag | ccc | ata | ttc | cct | gcc | 1222 |
| Met | Leu | Val | Glu | Thr | Ala | Gln | Glu | Arg | Asn | Glu | Pro | Ile | Phe | Pro | Ala |     |
|     |     |     |     | 280 |     |     |     |     | 285 |     |     |     |     | 290 |     |     |
| ctg | ata | tac | tca | tct | gcc | atg | gtg | tgg | acg | gtt | ggc | atg | gcg | aag | ctg | 1270 |
| Leu | Ile | Tyr | Ser | Ser | Ala | Met | Val | Trp | Thr | Val | Gly | Met | Ala | Lys | Leu |     |
|     |     |     | 295 |     |     |     |     | 300 |     |     |     |     | 305 |     |     |     |
| gac | ccc | tcc | tct | cag | ggt | gcc | ctc | cag | ctc | ccc | tac | gac | ccg | gag | atg | 1318 |
| Asp | Pro | Ser | Ser | Gln | Gly | Ala | Leu | Gln | Leu | Pro | Tyr | Asp | Pro | Glu | Met |     |
|     |     | 310 |     |     |     |     | 315 |     |     |     |     | 320 |     |     |     |     |
| gaa | gaa | gac | tcc | tat | gac | agt | ttt | ggg | gag | cct | tca | tac | ccc | gaa | gtc | 1366 |
| Glu | Glu | Asp | Ser | Tyr | Asp | Ser | Phe | Gly | Glu | Pro | Ser | Tyr | Pro | Glu | Val |     |
|     | 325 |     |     |     |     | 330 |     |     |     |     | 335 |     |     |     |     |     |
| ttt | gag | cct | ccc | ttg | act | ggc | tac | cca | ggg | gag | gag | ctg | gag | gaa | gag | 1414 |
| Phe | Glu | Pro | Pro | Leu | Thr | Gly | Tyr | Pro | Gly | Glu | Glu | Leu | Glu | Glu | Glu |     |
| 340 |     |     |     |     | 345 |     |     |     |     | 350 |     |     |     |     | 355 |     |
| gag | gaa | agg | ggc | gtg | aag | ctt | ggc | ctc | ggg | gac | ttc | atc | ttc | tac | agt | 1462 |
| Glu | Glu | Arg | Gly | Val | Lys | Leu | Gly | Leu | Gly | Asp | Phe | Ile | Phe | Tyr | Ser |     |
|     |     |     |     | 360 |     |     |     |     | 365 |     |     |     |     | 370 |     |     |
| gtg | ctg | gtg | ggc | aag | gcg | gct | gcc | acg | ggc | agc | ggg | gac | tgg | aat | acc | 1510 |
| Val | Leu | Val | Gly | Lys | Ala | Ala | Ala | Thr | Gly | Ser | Gly | Asp | Trp | Asn | Thr |     |
|     |     |     | 375 |     |     |     |     | 380 |     |     |     |     | 385 |     |     |     |
| acg | ctg | gcc | tgc | ttc | gtg | gcc | atc | ctc | att | ggc | ttg | tgt | ctg | acc | ctc | 1558 |

```
                                -continued

Thr Leu Ala Cys Phe Val Ala Ile Leu Ile Gly Leu Cys Leu Thr Leu
        390                 395                 400 ctg ctg ctt gct gtg ttc aag aag gcg ctg ccc gcc ctc ccc atc tcc   1606
Leu Leu Leu Ala Val Phe Lys Lys Ala Leu Pro Ala Leu Pro Ile Ser
    405                 410                 415 atc acg ttc ggg ctc atc ttt tac ttc tcc acg gac aac ctg gtg cgg   1654
Ile Thr Phe Gly Leu Ile Phe Tyr Phe Ser Thr Asp Asn Leu Val Arg
420                 425                 430                 435 ccg ttc atg gac acc ctg gcc tcc cat cag ctc tac atc tga           1696
Pro Phe Met Asp Thr Leu Ala Ser His Gln Leu Tyr Ile
                440                 445 gggacatggt gtgccacagg ctgcaagctg cagggaattt tcattggatg cagttgtata   1756
gttttacact ctagtgccat atatttttaa gacttttctt tccttaaaaa ataaagtacg   1816
tgtttacttg gtgaggagga ggcagaacca gctctttggt gccagctgtt tcatcaccag   1876
actttggctc ccgctttggg gagcgcctcg cttcacggac aggaagcaca gcaggtttat   1936
ccagatgaac tgagaaggtc agattagggc ggggagaaga gcatccggca tgagggctga   1996
gatgcgcaaa gagtgtgctc gggagtggcc cctggcacct gggtgctctg gctggagagg   2056
aaaagccagt tccctacgag gagtgttccc aatgctttgt ccatgatgtc cttgttattt   2116
tattgccttt agaaactgag tcctgttc                                     2144

<210> SEQ ID NO 2
<211> LENGTH: 2002
<212> TYPE: DNA
<213> ORGANISM: Homo sapiens
<220> FEATURE:
<221> NAME/KEY: CDS
<222> LOCATION: (350)..(724)
<223> OTHER INFORMATION:

<400> SEQUENCE: 2
gcatttccag cagtgaggag acagccagaa gcaagctatt ggagctgaag gaacctgaga    60
cagaagctag tccccctct gaattttact gatgaagaaa ctgaggccac agagctaaag    120
tgacttttcc caaggtcgcc cagcgaggac gtgggacttc tcagacgtca ggagagtgat   180
gtgagggagc tgtgtgacca tagaaagtga cgtgttaaaa accagcgctg ccctctttga   240
aagccaggga gcatcattca tttagcctgc tgagaagaag aaaccaagtg tccgggattc   300
agacctctct gcggccccaa gtgttcgtgg tgcttccaga ggcagggct atg ctc aca   358
                                                      Met Leu Thr
                                                       1 ttc atg gcc tct gac agc gag gaa gaa gtg tgt gat gag cgg acg tcc     406
Phe Met Ala Ser Asp Ser Glu Glu Glu Val Cys Asp Glu Arg Thr Ser
    5                   10                  15 cta atg tcg gcc gag agc ccc acg ccg cgc tcc tgc cag gag ggc agg     454
Leu Met Ser Ala Glu Ser Pro Thr Pro Arg Ser Cys Gln Glu Gly Arg
20                  25                  30                  35 cag ggc cca gag gat gga gag aac act gcc cag tgg aga agc cag gag     502
Gln Gly Pro Glu Asp Gly Glu Asn Thr Ala Gln Trp Arg Ser Gln Glu
                40                  45                  50 aac gag gag gac ggt gag gag gac cct gac cgc tat gtc tgt agt ggg     550
Asn Glu Glu Asp Gly Glu Glu Asp Pro Asp Arg Tyr Val Cys Ser Gly
            55                  60                  65 gtt ccc ggg cgg ccg cca ggc ctg gag gaa gag ctg acc ctc aaa tac     598
Val Pro Gly Arg Pro Pro Gly Leu Glu Glu Glu Leu Thr Leu Lys Tyr
        70                  75                  80 gga gcg aag cac gtg atc atg ctg ttt gtg cct gtc act ctg tgc atg     646
Gly Ala Lys His Val Ile Met Leu Phe Val Pro Val Thr Leu Cys Met
```

|   |   |   |   |   |   |   |   |   |   |   |   |   |   |     |
|---|---|---|---|---|---|---|---|---|---|---|---|---|---|----:|
|   |   |   |   |   | 85 |   |   |   | 90 |   |   |   | 95 |     |
| atc | gtg | gtg | gta | gcc | acc | atc | aag | tct | gtg | cgc | ttc | tac | aca gag aag | 694 |
| Ile | Val | Val | Val | Ala | Thr | Ile | Lys | Ser | Val | Arg | Phe | Tyr | Thr Glu Lys |  |
| 100 |   |   |   |   | 105 |   |   |   | 110 |   |   |   | 115 |  |

| aat | gga | cag | ctt | tca | tcc | atg | gct | ggt | tga | tcatgtcttc actgatgctg | 744 |
|-----|-----|-----|-----|-----|-----|-----|-----|-----|-----|----------------------|-----|
| Asn | Gly | Gln | Leu | Ser | Ser | Met | Ala | Gly |     |                      |     |
|     |     |     |     | 120 |     |     |     |     |     |                      |     |

```
ctgttcctct tcacctatat ctaccttggg gaagtgctca agacctacaa tgtggccatg    804
gactacccca ccctcttgct gactgtctgg aacttcgggg cagtgggcat ggtgtgcatc    864
cactggaagg gccctctggt gctgcagcag gcctacctca tcatgatcag tgcgctcatg    924
gccctagtgt tcatcaagta cctcccagag tggtccgcgt gggtcatcct gggcgccatc    984
tctgtgtatg atctcgtggc tgtgctgtgt cccaaagggc tctgagaat gctggtagaa   1044
actgcccagg agagaaatga gcccatattc cctgccctga tactcatc tgccatggtg     1104
tggacggttg gcatggcgaa gctggacccc tcctctcagg gtgccctcca gctcccctac   1164
gacccggaga tggaagaaga ctcctatgac agttttgggg agccttcata ccccgaagtc   1224
tttgagcctc ccttgactgg ctacccaggg gaggagctgg aggaagagga ggaaaggggc   1284
gtgaagcttg gcctcgggga cttcatcttc tacagtgtgc tggtgggcaa gcggctgcc   1344
acgggcagcg gggactggaa taccacgctg gcctgcttcg tggccatcct cattggcttg   1404
tgtctgaccc tcctgctgct tgctgtgttc aagaaggcgc tgcccgccct ccccatctcc   1464
atcacgttcg ggctcatctt ttacttctcc acggacaacc tggtgcggcc gttcatggac   1524
accctggcct cccatcagct ctacatctga gggacatggt gtgccacagg ctgcaagctg   1584
cagggaattt tcattggatg cagttgtata gttttacact ctagtgccat atatttttaa   1644
gacttttctt tccttaaaaa ataaagtacg tgtttacttg gtgaggagga ggcagaacca   1704
gctctttggt gccagctgtt tcatcaccag actttggctc ccgctttggg gagcgcctcg   1764
cttcacggac aggaagcaca gcaggtttat ccagatgaac tgagaaggtc agattagggc   1824
ggggagaaga gcatccggca tgagggctga gatgcgcaaa gagtgtgctc gggagtggcc   1884
cctggcacct gggtgctctg gctggagagg aaaagccagt tccctacgag gagtgttccc   1944
aatgctttgt ccatgatgtc cttgttattt tattgccttt agaaactgag tcctgttc     2002
```

<210> SEQ ID NO 3
<211> LENGTH: 1983
<212> TYPE: DNA
<213> ORGANISM: Homo sapiens

<400> SEQUENCE: 3

```
gcatttccag cagtgaggag acagccagaa gcaagctatt ggagctgaag gaacctgaga     60
cagaagctag tccccctct gaattttact gatgaagaaa ctgaggccac agagctaaag    120
tgactttcc caaggtcgcc cagcgaggac gtgggacttc tcagacgtca ggagagtgat    180
gtgagggagc tgtgtgacca tagaaagtga cgtgttaaaa accagcgctg ccctctttga    240
aagccaggga gcatcattca tttagcctgc tgagaagaag aaaccaagtg tccgggattc    300
agacctctct gcggccccaa gtgttcgtga aagccagga gaacgaggag gacggtgagg    360
aggaccctga ccgctatgtc tgtagtgggg ttccgggcg gccgccaggc ctggaggaag    420
agctgaccct caaatacgga gcgaagcacg tgatcatgct gtttgtgcct gtcactctgt    480
gcatgatcgt ggtggtagcc accatcaagt ctgtgcgctt ctacacagag aagaatggac    540
agctcatcta cacgacattc actgaggaca caccctcggt gggccagcgc ctcctcaact    600
```

```
ccgtgctgaa cacctctcatc atgatcagcg tcatcgtggt tatgaccatc ttcttggtgg    660
tgctctacaa gtaccgctgc tacaagttca tccatggctg gttgatcatg tcttcactga    720
tgctgctgtt cctcttcacc tatatctacc ttggggaagt gctcaagacc tacaatgtgg    780
ccatggacta ccccaccctc ttgctgactg tctggaactt cggggcagtg ggcatggtgt    840
gcatccactg gaagggccct ctggtgctgc agcaggccta cctcatcatg atcagtgcgc    900
tcatggccct agtgttcatc aagtacctcc cagagtggtc cgcgtgggtc atcctgggcg    960
ccatctctgt gtatgatctc gtggctgtgc tgtgtcccaa agggcctctg agaatgctgg   1020
tagaaactgc ccaggagaga atgagccca tattccctgc cctgatatac tcatctgcca   1080
tggtgtggac ggttggcatg gcgaagctgg accctcctc tcagggtgcc ctccagctcc   1140
cctacgaccc ggagatggaa gaagactcct atgacagttt tggggagcct tcatacccg   1200 aagtctttga gcctcccttg actggctacc aggggagga gctggaggaa gaggaggaaa   1260
ggggcgtgaa gcttggcctc ggggacttca tcttctacag tgtgctggtg gcaaggcgg   1320 ctgccacggg cagcggggac tggaatacca cgctggcctg cttcgtggcc atcctcattg   1380
gcttgtgtct gaccctcctg ctgcttgctg tgttcaagaa ggcgctgccc gccctcccca   1440
tctccatcac gttcgggctc atctttacct ctcccacgga caacctggtg cggccgttca   1500
tggacaccct ggcctcccat cagctctaca tctgagggac atggtgtgcc acaggctgca   1560
agctgcaggg aattttcatt ggatgcagtt gtatagtttt acactctagt gccatatatt   1620
tttaagactt ttcttctcctt aaaaaataaa gtacgtgttt acttggtgag gaggaggcag   1680
aaccagctct ttggtgccag ctgtttcatc accagacttt ggctcccgct ttggggagcg   1740
cctcgcttca cggacaggaa gcacagcagg tttatccaga tgaactgaga aggtcagatt   1800
agggcgggga gaagagcatc cggcatgagg gctgagatgc gcaaagagtg tgctcgggag   1860
tggcccctgg cacctgggtg ctctggctgg agaggaaaag ccagttccct acgaggagtg   1920
ttcccaatgc tttgtccatg atgtccttgt tattttattg cctttagaaa ctgagtcctg   1980
ttc                                                                 1983

<210> SEQ ID NO 4
<211> LENGTH: 1848
<212> TYPE: DNA
<213> ORGANISM: Homo sapiens

<400> SEQUENCE: 4
gcatttccag cagtgaggag acagccagaa gcaagctatt ggagctgaag gaacctgaga     60
cagaagctag tccccctct gaatttact gatgaagaaa ctgaggccac agagctaaag    120
tgacttttcc caaggtcgcc cagcgaggac gtgggacttc tcagacgtca ggagagtgat    180
gtgagggagc tgtgtgacca tagaaagtga cgtgttaaaa accagcgctg ccctctttga    240
aagccaggga gcatcattca tttagcctgc tgagaagaag aaaccaagtg tccgggattc    300
agacctctct gcggccccaa gtgttcgtgc aggtccaaaa tcactcaagg tggggagcct    360
cgaggagcag tcagggccgg gagcatcagc cccttgcctt ctccctcagc atctacacga    420
cattcactga ggacacaccc tcggtgggcc agcgcctcct caactccgtg ctgaacaccc    480
tcatcatgat cagcgtcatc gtggttatga ccatcttctt ggtggtgctc tacaagtacc    540
gctgctacaa gttcatccat ggctggttga tcatgtcttc actgatgctg ctgttcctct    600
tcacctatat ctaccttggg gaagtgctca agacctacaa tgtggccatg gactacccca    660
```

-continued

```
cccctcttgct gactgtctgg aacttcgggg cagtgggcat ggtgtgcatc cactggaagg   720
gccctctggt gctgcagcag gcctacctca tcatgatcag tgcgctcatg gccctagtgt   780
tcatcaagta cctcccagag tggtccgcgt gggtcatcct gggcgccatc tctgtgtatg   840
atctcgtggc tgtgctgtgt cccaaagggc ctctgagaat gctggtagaa actgcccagg   900
agagaaatga gcccatattc cctgccctga tatactcatc tgccatggtg tggacggttg   960
gcatggcgaa gctggacccc tcctctcagg gtgccctcca gctcccctac gacccggaga  1020
tggaagaaga ctcctatgac agttttgggg agccttcata ccccgaagtc tttgagcctc  1080
ccttgactgg ctacccaggg gaggagctgg aggaagagga ggaaaggggc gtgaagcttg  1140
gcctcgggga cttcatcttc tacagtgtgc tggtgggcaa gcggctgcc acgggcagcg  1200 gggactggaa taccacgctg gcctgcttcg tggccatcct cattggcttg tgtctgaccc  1260
tcctgctgct tgctgtgttc aagaaggcgc tgcccgccct ccccatctcc atcacgttcg  1320
ggctcatctt ttacttctcc acggacaacc tggtgcggcc gttcatggac accctggcct  1380
cccatcagct ctacatctga gggacatggt gtgccacagg ctgcaagctg cagggaattt  1440
tcattggatg cagttgtata gttttacact ctagtgccat atatttttaa gactttctt   1500 tccttaaaaa ataaagtacg tgtttacttg gtgaggagga ggcagaacca gctctttggt  1560
gccagctgtt tcatcaccag actttggctc ccgctttggg gagcgcctcg cttcacggac  1620
aggaagcaca gcaggtttat ccagatgaac tgagaaggtc agattagggc ggggagaaga  1680
gcatccggca tgagggctga gatgcgcaaa gagtgtgctc gggagtggcc cctggcacct  1740
gggtgctctg gctggagagg aaaagccagt tccctacgag gagtgttccc aatgctttgt  1800
ccatgatgtc cttgttattt tattgccttt agaaactgag tcctgttc                1848
```

<210> SEQ ID NO 5
<211> LENGTH: 375
<212> TYPE: DNA
<213> ORGANISM: Homo sapiens
<220> FEATURE:
<221> NAME/KEY: CDS
<222> LOCATION: (1)..(375)
<223> OTHER INFORMATION:

<400> SEQUENCE: 5

```
atg ctc aca ttc atg gcc tct gac agc gag gaa gaa gtg tgt gat gag       48
Met Leu Thr Phe Met Ala Ser Asp Ser Glu Glu Glu Val Cys Asp Glu
1               5                   10                  15 cgg acg tcc cta atg tcg gcc gag agc ccc acg ccg cgc tcc tgc cag       96
Arg Thr Ser Leu Met Ser Ala Glu Ser Pro Thr Pro Arg Ser Cys Gln
            20                  25                  30 gag ggc agg cag ggc cca gag gat gga gag aac act gcc cag tgg aga      144
Glu Gly Arg Gln Gly Pro Glu Asp Gly Glu Asn Thr Ala Gln Trp Arg
        35                  40                  45 agc cag gag aac gag gag gac ggt gag gag gac cct gac cgc tat gtc      192
Ser Gln Glu Asn Glu Glu Asp Gly Glu Glu Asp Pro Asp Arg Tyr Val
    50                  55                  60 tgt agt ggg gtt ccc ggg cgg ccg cca ggc ctg gag gaa gag ctg acc      240
Cys Ser Gly Val Pro Gly Arg Pro Pro Gly Leu Glu Glu Glu Leu Thr
65                  70                  75                  80 ctc aaa tac gga gcg aag cac gtg atc atg ctg ttt gtg cct gtc act      288
Leu Lys Tyr Gly Ala Lys His Val Ile Met Leu Phe Val Pro Val Thr
                85                  90                  95 ctg tgc atg atc gtg gtg gta gcc acc atc aag tct gtg cgc ttc tac      336
Leu Cys Met Ile Val Val Val Ala Thr Ile Lys Ser Val Arg Phe Tyr
            100                 105                 110
```

```
aca gag aag aat gga cag ctt tca tcc atg gct ggt tga              375
Thr Glu Lys Asn Gly Gln Leu Ser Ser Met Ala Gly
        115                 120
```

<210> SEQ ID NO 6
<211> LENGTH: 124
<212> TYPE: PRT
<213> ORGANISM: Homo sapiens

<400> SEQUENCE: 6

```
Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
                100                 105                 110

Thr Glu Lys Asn Gly Gln Leu Ser Ser Met Ala Gly
            115                 120
```

<210> SEQ ID NO 7
<211> LENGTH: 20
<212> TYPE: DNA
<213> ORGANISM: Homo sapiens

<400> SEQUENCE: 7
attcagacct ctctgcggcc                                             20

<210> SEQ ID NO 8
<211> LENGTH: 20
<212> TYPE: DNA
<213> ORGANISM: Homo sapiens

<400> SEQUENCE: 8
gcatggtgtg catccactgg                                             20

<210> SEQ ID NO 9
<211> LENGTH: 20
<212> TYPE: DNA
<213> ORGANISM: Homo sapiens

<400> SEQUENCE: 9
ggaccactct gggaggtact                                             20

<210> SEQ ID NO 10
<211> LENGTH: 20
<212> TYPE: DNA
<213> ORGANISM: Homo sapiens

<400> SEQUENCE: 10
gctggcacca aagagctggt                                             20